United States Patent [19]

Redmore et al.

[11] 4,051,029

[45] Sept. 27, 1977

[54] PROCESS OF INHIBITING SCALE FORMATION WITH MIXTURES OF THIO-, OXYGEN OR THIO-OXYGEN PHOSPHATES AND PYROPHOSPHATES

[75] Inventors: Derek Redmore, Ballwin; Alfred E. Woodson, Festus, both of Mo.

[73] Assignee: Petrolite Corporation, St. Louis, Mo.

[21] Appl. No.: 590,448

[22] Filed: June 26, 1975

Related U.S. Application Data

[62] Division of Ser. No. 272,676, July 17, 1972, Pat. No. 3,909,447.

[51] Int. Cl.$^2$ ................................................ C02B 5/06
[52] U.S. Cl. ...................................... 210/58; 252/175; 252/180; 252/181; 252/389 A; 21/2.7 R; 21/2.7 A; 21/2.5 A
[58] Field of Search ............... 252/180, 181, 389 A, 252/175; 21/2.7 R, 2.7 A, 2.5 A; 210/58

[56] References Cited

U.S. PATENT DOCUMENTS

| 3,462,365 | 8/1969 | Vogelsang | 252/180 |
|---|---|---|---|
| 3,488,289 | 1/1970 | Tate | 252/180 |
| 3,510,436 | 5/1970 | Silverstein et al. | 252/389 X |
| 3,597,352 | 8/1971 | Stanford et al. | 252/180 |
| 3,654,170 | 4/1972 | Woodson | 252/175 |
| 3,668,138 | 6/1972 | Hoover et al. | 252/181 |
| 3,723,333 | 3/1973 | Freybold | 252/175 |
| 3,859,396 | 1/1975 | Alink | 252/175 |

*Primary Examiner*—Mayer Weinblatt
*Attorney, Agent, or Firm*—Derek Redmore; Alfred E. Woodson

[57] ABSTRACT

Mixtures of Thiophosphates, pyrophosphates containing both oxygen and sulfur, and oxygen phosphates are effective as scale inhibitors. The mixtures are synergistically more effective as scale inhibitors than each component individually.

These synergistic mixtures are also effective for other uses such as for inhibiting corrosion, particularly in aqueous and/or oxygenated systems.

14 Claims, No Drawings

PROCESS OF INHIBITING SCALE FORMATION WITH MIXTURES OF THIO-, OXYGEN OR THIO-OXYGEN PHOSPHATES AND PYROPHOSPHATES

This application is a division of patent application Ser. No. 272,626 filed July 17, 1972, now U.S. Pat. No. 3,909,447, issued Sept. 30, 1975.

One of the most difficult problems in the field of corrosion inhibition is that of preventing and/or inhibiting corrosion in oxygenated aqueous sytems such as in water floods, cooling towers, drilling muds, air drilling, auto radiator systems, etc.

Many corrosion inhibitors capable of performing in non-aqueous systems and/or non-oxygenated systems perform poorly in aqueous and/or oxygenated systems (i.e. aerobic systems).

In application Ser. No. 821,144, of Pedmore, Outlaw and Martin filed May 1, 1969, now abandoned there is described and claimed dithiophosphoric acids and the use thereof as corrosion inhibitors in aqueous and/or oxygenated systems.

Although the reaction of simple alcohols with $P_2S_5$ primarily proceeds according to the following equation

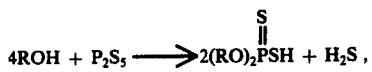

with minor side reactions, Ser. No. 874,713 filed Nov. 6, 1969, now abandoned, which is a continuation in part of Ser. No. 821,144 disclosed that when certain alcohols are reacted, for example higher alkyl alcohols, phenols, oxyalkylated alcohols, etc., side reactions predominate. Thus,

initially formed from such alcohols yields through anhydride formation and/or isomerization pyrophosphates as illustrated in the following equations:

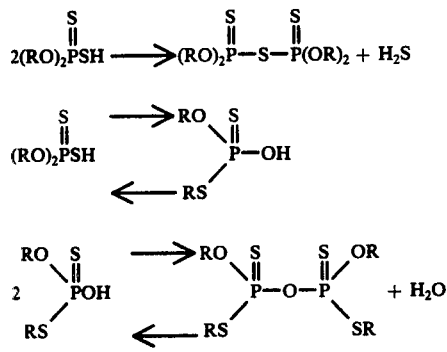

Although the ratio of products will vary with reactants, properties, reaction conditions, etc., a typical reaction product ratio of products formed by reacting an oxyalkylated alcohol with $P_2S_5$ is as follows:

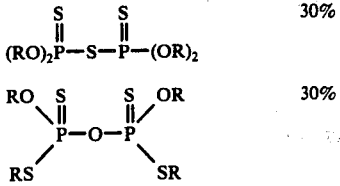

Thus, the major part of the product comprises anhydrides and/or isomerized anhydrides (i.e., pyrophosphates) which are excellent corrosion inhibitors, etc.

The production of pyrophosphates which contain both sulfur and oxygen of the formula

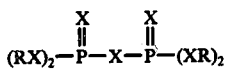

where X = O or S in substantial amounts is unexpected since the reaction of simple alcohols, such as lower alkyl alcohols ROH, with $P_2S_5$ yields little, if any, pyrophosphates. See Houben-Weyl, Phosphorous Compounds, Part II, p. 684, published by Georg Thieme Verlag in 1964. In contrast where the more complex alcohols are reacted, for example, oxyalkylated alcohols such as of the formula $R'(OA)_nOH$ where R' is alkyl, cycloalkyl, alkenyl, aryl, aralkyl, alkaryl, heterocyclic, etc., higher alkyl alcohols such as where R has at least seven carbon atoms, etc., pyrophosphates comprise a substantial part of the resultant reaction product. In general, the yield of pyrophosphate is increased by prolonged heating. Thus, in order to increase the yield of pyrophosphates, in contrast to reaction time of 1-3 hours for the dialkyl dithiophosphates, reaction times at elevated temperatures of more than 3 hours, such as 3-15 or more hours, enhance the yield of pyrophosphates. The use of vacuum or reduced pressure during this heating period also enhances the yield of pyrophosphates, e.g., 20-150 mm.

The general procedure for reacting alcohols with $P_2S_5$ to form O,O-disubstituted dithiophosphoric acids is to continue reaction until most of the $P_2S_5$ has dissolved and the evolution of $H_2S$ has subsided. In contrast, the general procedure for preparing the pyrophosphates is to continue the reaction past this point so as to shift the equilibrium in favor of converting the dithiophosphoric acids to the pyrophosphate.

Since the crude reaction products contain O,O-disubstituted dithiophosphoric acids

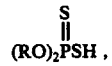

salts of these can also be prepared.

The salts are prepared by the simple neutralization of the acid with a suitable salt-forming base or by double decomposition. The salt moiety may be for example, Cu, Ni, Al, Pb, Hg, Cd, Sn, Zn, Mg, Na, K, $NH_4$, amine, Co, Sr, Ba, etc. These may be prepared from the corresponding oxide, hydroxide, carbonate, sulfide, etc. An alternative to the preparation of salts is to use a simple combination of dithiophosphate with a metal salt such as zinc chloride, zinc sulfate, etc. This allows the use of higher stoichiometric amounts of metal ions to dithiophosphate, such as from 1:1 to 4:1.

The alcohols employed to prepare the ester may be oxyalkylated alcohols for example of the formula

R'(OA)$_n$OH where OA is a moiety derived from an alkylene oxide and n is a number for example from about 1-100 or more, for example from 1-50, such as from 1-25, but preferably from 1-10.

The alkylene oxides employed herein are 1,2-alkylene oxides of the formula

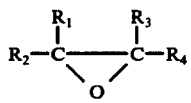

where R$_1$, R$_2$, R$_3$ and R$_4$ are selected by the group consisting of hydrogen, aliphatic, cycloaliphatic, aralkyl, etc. for example ethylene oxide, propylene oxide, butylene oxide, amylene oxide, octylene oxide, styrene oxide, methyl styrene oxide, cyclohexene oxide (where R$_1$ and R$_3$ are joined to make a ring), etc.

The alkylene oxide may be added to form homo polymer, stepwise to form block polymers, as mixtures to form heteropolymers or combinations thereof, etc.
For example

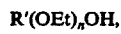
R'(OEt)$_n$OH,

R'(OPr)$_n$OH,

R'(OEt)$_n$(OPr)$_m$OH,

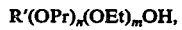
R'(OPr)$_n$(OEt)$_m$OH,

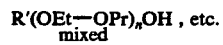
R'(OEt—OPr)$_n$OH, etc.
 mixed

One of the preferred classes of such alcohols is R'(OEt)$_{0.5-10}$OH, where R' has from about 8-18 carbon atoms.

These phosphates derived from P$_2$S$_5$ are designated in the following discussion as Type A. These materials are significantly improved as corrosion inhibitors and scale inhibitors by mixing with non-sulfur containing phosphates designated as Type B.

The Type B phosphates preferredly are formed by phosphorylation of the alcohols described above using reagents as phosphorus pentoxide, poly phosphoric acid, phosphorus oxychloride, etc.

Examples 1-5 illustrate the thiophosphate materials and Examples 6-14 the non-sulfur containing phosphate esters.

The reaction of alcohols with P$_2$O$_5$ is carried out in the conventional manner. It may be summarized by the following idealized equation

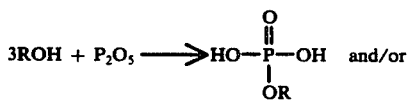

3ROH + P$_2$O$_5$ → HO—P(=O)—OH and/or
       |
       OR

HO—P(=O)—OR
   |
   OR

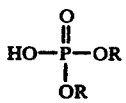

In general, the alcohols employed in preparing the oxygen phosphates are the same as that employed with the thiophosphates.

The following examples illustrate thiophosphate compounds: (Type A)

EXAMPLE 1

The alcohol derived from the addition of 1 weight of ethylene oxide to "Alfol" 8-10 (576g; 2 mole) was stirred at 25-40° P$_2$S$_5$ (Illg; 0.5 mole) was added during 2 hours. The reaction was heated to 105°-109° at a pressure of 70 mm for 9½ hours. Upon cooling the product, 657 g. was obtained as a pale yellow liquid. Sulfur analysis, 9.06%; phosphorus, 4.77%; acid value 0.62 meg/g. The product was neutralized with anhydrous ammonia.

EXAMPLE 2

The alcohol derived from the addition of 1 weight of ethylene oxide to "Alfol" 8-10 (288g; 1 mole) was stirred at 70°-75° C. while P$_2$S$_5$ (55g; 0.25 mole) was added in 60 mins. The reaction mixture was heated at 100°-110° under reduced pressure (75mm) for 8 hours as H$_2$S was evolved. The resulting acid was neutralized with dimethyl aniline.

EXAMPLE 3

The alcohol derived from the addition of 2 weights of ethylene oxide to "Alfol" 8-10 (432g; 1 mole) was stirred at 70°-75° C. during the addition of P$_2$S$_5$ (55g; 0.25 mole). The addition was complete in 60 min. and heating was continued at 100°-110° for 10 hours to complete H$_2$S evolution. Nuetralization was effected by the addition of anhydrous ammonia.

The following examples use higher P$_2$S$_5$ ratios.

EXAMPLE 4

The alcohol derived from the addition of 1 weight of ethylene oxide to "Alfol" 8-10 (288g; 1 mole) was heated at 75°-80° C while P$_2$S$_5$ (70g; 0.315 mole) was added during 45 min. The mixture was heated at 100°-105° C. for 3 hours at which time H$_2$S evolution was complete. After cooling to 70° tributylamine (42g) was added and the mixture stirred at 70°-75° for 1 hour to complete neutralization.

EXAMPLE 5

The alcohol derived from the addition of 1 weight of ethylene oxide to "Alfol" 8-10 (288g; 1 mole) was heated at 75-80° C. with stirring while P$_2$S$_5$ (70g; 0.315 mole) was added in 45 min. The mixture was heated at 100°-110° for 4 hours to complete evolution of H$_2$S. After cooling to 65° C. anhydrous ammonia (5g) was added to effect neutralization.

The following examples illustrate non-sulfur containing phosphates (Type B).

EXAMPLE 6

To the alcohol derived from the addition of 0.8 weight of ethylene oxide to "Alfol" 8-10 (180g; 0.7 mole) was carefully added phosphorus pentoxide (33g; 0.23 mole). The reaction mixture spontaneously rose to 90° upon this addition. The reaction was completed by heating at 125° C. for 1 hour to yield a straw colored liquid.

EXAMPLE 7

To the alcohol derived from 2-ethylhexanol with 1 weight of ethylene oxide added (130g; 1 mole) was added phosphorus pentoxide (47g; 0.33 mole) during 10 mins. This addition resulted in an exotherm taking the temperature to 75°. The phosphorylation was completed by heating at 110° for 1½ hours yielding a pale yellow liquid.

EXAMPLE 8

To the alcohol derived from the addition of 1 weight of ethylene oxide to "Alfol" 8-10 (130g; 0.45 mole) was added polyphosphoric acid (77g; 0.45 mole) in 15 mins. This addition resulted in a temperature increase to 70°. The reaction was then heated at 110°-112° for 1 hour to complete the reaction. The product was a viscous amber liquid.

The following tables present additional illustrative examples:

| Example No. | Alcohol | Phosphorylating Reagent | Procedure |
|---|---|---|---|
| 9 | "Alfol"8-10+1 weight EtO* | $P_2O_5$ | Example 6 |
| 10 | "Alfol"14+0.5 weight EtO | $P_2O_5$ | Example 6 |
| 11 | "Alfol"8-10+0.8 weight EtO | Polyphosphoric Acid | Example 8 |
| 12 | "Alfol"14+0.5 weight EtO | Polyphosphoric Acid | Example 8 |
| 13 | "Alfol"8-10 | $P_2O_5$ | Example 6 |
| 14 | 2-ethyl hexanol | $P_2S_5$ | Example 6 |

*EtO = Ethylene Oxide
"Alfol" — linear alcohols number indicates predominant carbon chain.

The weight ratio of thiophosphate and/or pyrophosphate to phosphate can vary widely for example from about 10:1 to 1:10, such as from about 5:1 to 1:5 for example from about 3:1 to 1:3, but preferably from about 2:1 to 1:2.

In addition we have discovered that the presence of zinc in the compositions of this invention further enhances the synergism of the thio and non-thio phosphates and pyrophosphates of this invention. Zinc is employed in amounts from about 0.5 to 50% by weight based on the active ingredients, such as from about 1 to 40 for example from about 1 to 40 but preferably from about 5 to 25%.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to be a storage reservois from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system." It the water is recirculated in a closed system without substantial aeration, the secondary recovery method is referred to herein as a "closed water flooding system."

Because of the corrosive nature of oil field brines, to ecomically produce oil by water flooding, it is necessary to prevent or reduce corrosion since corrosion increases the cost thereof by making it necessary to repair and replace such equipment at frequency intervals.

We have now discovered a method of preventing corrosion in systems containing a corrosive aqueous media, and most particularly in systems containing brines, which is characterized by employing the compositions of this invention.

We have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the reducing compound, sufficient to prevent corrosion, in concentrations of about 10 p.p.m. to 10,000 p.p.m., or more, for example, about 50 to 5000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 100 p.p.m. Since these compounds are themselves inexpensive and are used in low concentrations, they enhance the success of a flood operation by lowering the cost thereof.

In addition, these compounds are not sensitive to oxygen content of the water and these are effective corrosion inhibitors in both open water flooding systems and closed water flooding systems.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

USE IN FLUIDS FOR DRILLING WELLS

This phase of the invention relates to the use of the compounds of this invention as corrosion inhibitors in producing an improved drilling fluid useful in drilling oil and gas wells.

Fluids commonly used for the drilling of oil and gas wells are of two general types: water-base drilling fluids comprising, for example, a clay suspended in water, and oil-base drilling fluids comprising, for example, a clay or calcium carbonate suspended in mineral oil.

A third type of drilling fluid which has recently been developed, is one of oil-in-water or water-in-oil emulsion, for example, emulsions of mineral oil in water or water in mineral oil formed by means of emulsifiers such as sulfuric acid; Turkey-red oil; soaps of fatty acids, for example, sodium oleate; emulsoid colloids, for example starch, sodium alginate, etc. Varying amounts of finely divided clay, silica, calcium carbonate, blown asphalt and other materials may be added to these emulsions to improve their properties and control their weight.

We have discovered that the compositions of this invention can be employed as a corrosion inhibitor in drilling fluids.

USE IN AIR DRILLING

It has long been conventional practice in drilling deep bore holes to circulate a drilling mud down through the drill stem and up through the bore hole between the wall of the bore hole and the drill stem for the removal of chips or cuttings from the bore hold and to provide support for the wall of the bore hole. More recently, in the drilling of holes in which wall support provided by drilling mud is not employed, drilling has been carried out with the use of air for chip removal. Such drilling is not only normally faster than mud drilling but is indispensable in areas where the supply of water is limited or when drilling through cavernous formations into which the drilling mud flows and becomes lost.

The increasing popularity of air or gas drilling has come about not only because this method of drilling is frequently faster, as noted above, but for the additional reasons that the drill bits last longer, the provision and handling of water under wide ranges of temperature conditions is avoided, boring samples are easily observed when they are not mixed with mud, and there is no loss involved as in the case of mud drilling when drilling through cavernous formations. Furthermore, prompt removal of water entering the hole maintains a dry hole and the likelihood of wall collapse is thereby reduced.

In a typical air drilling operation there may be provided, for example, an up-flow of air in the bore hole having a velocity of the order of 3,000 feet per minute. This flow of air upwardly through the bore hole, which is produced by air pumped downwardly through the drill steam, provides adequate removal of cuttings. The air is delivered to the drill stem at pressures of 20 to 60 lbs. per square inch and for dewatering or for breaking obstructions, as will be hereinafter described, the pressures may be increased to 180 to 200 lbs. or more per square inch.

Air drilling operations are frequently hampered by the inflow of water into the bore hole when the drill bit is penetrating a water bearing stratum or when the bore hole has passed through a water bearing stratum that has not been cased. Normally, if drilling proceeds uninterruptedly both before and during penetration into a water bearing stratum, the flow of air is sufficient to blow the water out of the bore hole along with the cuttings and drilling dirt. There are, however, two major problems encountered in air drilling when water is entering the bore hole. The first problem occurs when there is a small inflow of water sufficient to cause a dampening of the cuttings which, under certain conditions, will then ball-up, clogging and sometimes jamming the drill bit. The second problem is encountered when there is a substantial amount of water remaining in the bottom of the bore hole during drilling causing a sloughing of the side wall of the bore hole. This latter condition may arise even though the water entering the bore hole is being blown out of the hole as fast as it enters. If there is a substantial inflow of water or if there is a substantial flow of water past a region of the bore susceptible to this condition, the water passing that region of the bore hole may cause a sloughing of the side wall.

The addition of foam forming materials to the air flow when air drilling is employed in conjunction with sufficient water to provide foaming gives rise to numerous advantages in drilling operations. The water may be introduced either through a water bearing stratum being penetrated by the drill bit or, alternatively, if the hole is dry, water may be introduced from the surface of the earth through the drill stem in conjunction with the delivery of compressed air and foam forming material through the drill stem to the drill bit. In either case the water may be said to be existing in the bore hole, and drilling operations are described in U.S. Pat. No. 3,130,798.

The compositions of this invention can be employed as a corrosion inhibitor in a drilling system.

The compositions of this invention may also be added to other aqueous and/or oxygenated systems such as steam generating systems, water circulating systems such as in cooling towers, in automobile radiators, in diesel locomotive engines, in boiler water, sea-water ship ballast, etc.

The amount of the compositions of the invention to be employed as a corrosion inhibitor can vary widely depending upon particular compounds, the particular system, the amounts of oxygen present, etc. We may employ concentrations of from about 0.5 to 5,000 p.p.m., such as from about 4 to 4,000 p.p.m., for example from about 20 to 2,000 p.p.m., but preferably from about 100 to 1,000 p.p.m. The optimum amount, to be determined in each instance, which will depend on function and economics, can be lesser or greater than the above amounts under proper conditions.

USE IN COOLING WATER

The compositions of this inventin can also be employed in cooling towers since they are particularly effective in inhibiting corrosion in such systems. This is illustrated by the following examples.

Corrosion Tests

Corrosion tests were made using sand blasted 1020 mild steel coupons monitored by a polarization resistance meter, a PAIR instrument described in U.S. Pat. No. 3,406,101. The tests were in 1000 ml beakers stirred with a magnetic stirring bar and maintained at 20°. The fluids were kept air saturated by means of an air inlet below the liquid surface. The fluids used were made up to simulate typical cooling water compositions and are as follows: Composition designated 10X is prepared as follows:

| | |
|---|---|
| Sodium bicarbonate | 2.9 g |
| Magnesium sulfate | 5.7 g |
| Calcium chloride | 5.2 g |
| Calcium sulfate | 7.2 g |
| Sodium sulfate | 8.3 g | made up to 5 gallons with deionized water

Composition designated 1X is made diluting 1 part 10X to 10 parts. Protection is calculated in the usual manner from corrosion rate ($R_1$) of fluids without inhibitors and corrosion rate ($R_2$) in presence of a particular inhibitor according to the formula:

$$\frac{R_1 - R_2}{R_1} \times 100 = \% \text{ protection}$$

Table 1 below shows the inhibitor performance of the thio phosphate compositions (Type A).

Table 1

| Inhibitor | Concentration p.p.m. | Water Composition | Protection 8 hrs. | Protection 24 hrs. |
|---|---|---|---|---|
| Example 1 | 25 | 1X | 10% | 5% |
| Example 4 | 50 | 1X | 30% | 30% |
| Example 1 | 100 | 10X | 20% | 37% |
| Example 4 | 100 | 10X | 18% | 47% |

Table 2 shows the inhibitor performance of non-sulfur containing phosphate compositions (Type B).

Table 2

| Inhibitor | Concentration p.p.m. | Water Composition | Protection 8 hrs. | Protection 24 hrs. |
|---|---|---|---|---|
| Example 6 | 50 | 1X | 71% | 17% |
| Example 6 | 100 | 1X | 78% | 63% |
| Example 8 | 50 | 1X | 51% | 58% |
| Example 8 | 100 | 1X | 60% | 52% |
| Example 9 | 50 | 1X | 80% | 13% |
| Example 9 | 100 | 1X | 86% | 87% |
| Example 11 | 100 | 1X | 36% | 34% |
| Example 11 | 100 | 10X | 41% | 33% |
| Example 14 | 100 | 10X | 66% | 62% |

Table 3 shows the synergistic behaviour of mixtures of the compositions of Type A and Type B as corrosion inhibitors.

Table 3

| Inhibitor Combination Type B (p.p.m.) | Type A (p.p.m.) | Water Composition | Protection at 8 hrs. | 24 hrs. |
|---|---|---|---|---|
| Example 11 (66) | Example 1 (33) | 1X | 86% | 89% |
| Example 11 (33) | Example 1 (16) | 1X | — | 77% |
| Example 11 (75) | Example 1 (25) | 1X | 89% | 87% |
| Example 11 (50) | Example 1 (50) | 1X | 97% | 96% |
| Example 11 (80) | Example 1 (20) | 1X | 93% | 85% |
| Example 6 (66) | Example 1 (33) | 1X | 83% | 85% |
| Example 9 (66) | Example 1 (33) | 1X | 81% | 93% |
| Example 11 (66) | Example 4 (33) | 1X | 80% | 91% |
| Example 11 (75) | Example 1 (25) | 10X | 86% | 91% |
| Example 11 (66) | Example 1 (33) | 10X | 87% | 90% |
| Example 11 (80) | Example 1 (20) | 10X | 85% | 96% |
| Example 6 (66) | Example 1 (33) | 10X | — | 40% |
| Example 9 (66) | Example 1 (33) | 10X | — | 43% |
| Example 11 (75) | Example 4 (25) | 10X | 75% | 82% |
| Example 6 (75) | Example 4 (25) | 10X | 60% | 81% |

Table 4 shows that the addition of zinc ions can exert a further synergistic effect on the combinations of Table 3.

Table 4

| Inhibitor Combination Type B (p.p.m.) | Type A (p.p.m.) | Zinc p.p.m. | Water Composition | Protection at 8 hrs. | 24 hrs. |
|---|---|---|---|---|---|
| Example 11 (60) | Example 1 (30) | 10 | 1X | 77% | 68% |
| Example 11 (50) | Example 1 (25) | 25 | 1X | 88% | 92% |
| Example 11 (60) | Example 1 (30) | 10 | 10X | 98% | 100% |
| Example 11 (50) | Example 1 (25) | 25 | 10X | 98% | 99% |

USE AS SCALE INHIBITORS

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

More than 25 years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May, 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about 10 to 1, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound is added to a solution containing the anion of the relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which threshold active compounds sequester the cations of relatively insoluble compounds and the low concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compound that has sequestering powers does not predictably have threshold inhibiting properties. For example, ethylene diamine tetracetic acid salts are powerful sequesterants but have no threshold activities.

We have now discovered a process for inhibiting scale such as calcium, barium and magnesium carbonate, sulfate, silicate, etc., scale which comprises employing threshold amounts of the compositions of this invention, i.e., mixtures of thiophosphate, pyrophosphate containing both oxygen and sulfur, and oxygen phosphate esters of the alkanols and/or oxyalkylated alcohols described above Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 p.p.m., and are preferably used in concentrations of less than 25 p.p.m.

The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 p.p.m. to about 50,000 p.p.m. of scale-forming salts. The compounds of the present invention effectively inhibit scale formation when present in an amount of from 0.1 to about 100 p.p.m., and preferably 0.2 to 25 p.p.m. wherein the amounts of the inhibitor are based upon the total aqueous sytem. There does not appear to be a concentration below which the compounds of the present invention are totally ineffective. A very small amount of the scale inhibitor is effective to a correspondingly limited degree, and the threshold effect is obtained with less than 0.1 p.p.m. There is no reason to believe that this is the minimum effective concentration. The scale inhibitors of the present invention are effective in both brime, such as sea water, and acid solutions.

Calcium Scale Inhibition Test

The procedure utilized to determine the effectiveness of our scale inhibitors in regard to calcium scale is as follows:

Several 50 ml. samples of a 0.04 sodium bicarbonate solution are placed in 100 ml. bottles. To these solutions is added the inhibitor in various known concentrations. 50 ml. samples of a 0.02 M $CaCl_2$ solution are then added.

A total hardness determination is then made on the 50—50 mixture utilizing the well known Schwarzenbach titration. The samples are placed in a water bath and heated at 180° F. 10 ml. samples are taken from each bottles at 2 and 4 hour periods. These samples are filtered through millipore filters and the total hardness of the filtrates are determined by titration.

$$\frac{\text{Total hardness after heating}}{\text{Total hardness before heating}} \times 100 - \% \text{ inhibition}$$

Table 5 describes the scale inhibition test results obtained.

Table 5
Inhibition of scale formation from a CaCO₃ solution at 180° F. for 4 hours (200 p.p.m. CaCO₃).

| Composition | Concentration | % Scale Inhibition |
|---|---|---|
| Example 1 (1 part) + Example 11 (2 parts) | 5 p.p.m. | 45 |
| Example 1 (1 part) + Example 11 (2 parts) | 50 p.p.m. | 60 |
| Example 4 (1 part) + Example 11 (1 part) | 50 p.p.m. | 48 |
| Example 4 (1 part) + Example 11 (2 parts) | 50 p.p.m. | 58 |
| Example 4 (1 part) + Example 7 (3 parts) | 5 p.p.m. | 36 |
| Example 4 (1 part) + Example 7 (3 parts) | 50 p.p.m. | 44 |
| Commercial phosphate | 50 p.p.m. | 40 |
| Commercial phosphonate | 50 p.p.m. | 42 |

As is quite evident, other phosphates, thiophosphates and pyrophosphates will be constantly developed which could be useful in our invention. It is, therefore, not only impossible to attempt a comprehensive catalogue of such compositions, but to attempt to describe the invention in its broader aspects in terms of specific chemical names used would be too voluminous and unnecessary since one skilled in the art could by following the description of the invention herein select a useful pyrophosphate. This invention lies in the use of suitable phosphates of this invention in conjunction with suitable salts where appropriate as corrosion inhibitors in aqueous and/or oxygenated systems and their individual compositions are important only in the sense that their properties can affect this function. To precisely define each specific useful phosphate and aqueous sytem in light of the present disclosure would merely call knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific phosphates suitable for this invention by applying them in the process set forth herein. In analogy to the case of a machine, wherein the use of certain materials of construction or dimensions of part would lead to no practical useful result, various materials will be rejected as inapplicable where others would be operative. We can obviously assume that no one will wish to use a useless phosphate nor will be misled because it is possible to misapply the teachings of the present disclosure to do so. Thus, any phosphate or mixtures containing them that can perform the function stated herein can be employed.

The alcohols employed in this invention are the same alcohols employed in Ser. No. 821,144 and 874,713. They are alkanols, preferably oxyalkylated, and preferably having at least about 7 carbon atoms, for example about 7-20 carbon atoms, but preferably having about 8-14 carbon atoms.

The preferred alcohols are "Alfol" alcohols which are linear alkanols. The number associated with the trademark indicates the predominant carbon length. Thus in "Alfol" 8-10 the predominant carbon chain is between 8 and 10 carbon atoms. In "Alfol" 14 the predominant carbon length is 14. For optimum properties, these alcohols are oxyalkylated with about 0.5-10 moles of an alkylene oxide, preferably about 1 to 2 moles of ethylene oxide.

We claim:

1. A process of inhibiting scale formation in a system which comprises treating said system with a composition comprising a mixture of thiophosphate, pyrophosphate containing both oxygen and sulfur, and oxygen phosphate esters of alcohols selected from the group consisting of alkanols having at least seven carbon atoms and alcohols of the formula $R'(OA)_nOH$ where $R'$ is alkyl, cycloalkyl, alkenyl, aryl, aralkyl, alkaryl, or heterocyclic, $A$ is an alkylene moiety and $n$ is from 1 to 100, said pyrophosphate esters being the major part of the combined thiophosphate and pyrophosphate esters and the weight ratio of said combined esters to the oxygen phosphate esters being from about 10:1 to 1:10.

2. The process of claim 1 where said acid esters are those of alkanols or oxyalkylated alkanols, said alkanols having about 7 to 20 carbon atoms.

3. The process of claim 2 where the composition also contains zinc ions.

4. The process of claim 2 where the group OA is derived from ethylene oxide.

5. The process of claim 4 where the composition also contains zinc ions.

6. The process of claim 2 where A is ethylene, R' has from about 8-18 carbon atoms and said alcohol is prepared by reacting an alkanol of about 8-18 carbon atoms with 0.5 to 10 moles of ethylene oxide per mole of alkanol.

7. The process of claim 6 where the composition also contains zinc ions.

8. The process of claim 6, wherein said alkanol is a linear alkanol of about 8-14 carbon atoms.

9. The process of claim 8, wherein the composition also contains zinc ions.

10. The process of claim 1 where the composition also contains zinc ions.

11. The process of claim 1 wherein said composition comprises

I. a mixture of different compounds, each having the formula,

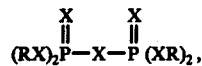

II. a compound or mixture of compounds, each having the formula

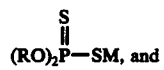

III. a compound or mixture of compounds selected from the group consisting of compounds having the formula,

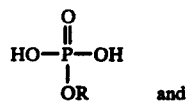

compounds having the formula

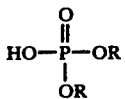

where X is oxygen and sulfur, each of said different compounds in I containing both oxygen and sulfur, wherein M is hydrogen, a metal, ammonium or an amine and R is alkyl or R'(OA)$_n$ as defined in claim 1, with the further limitation that said compounds are esters of alkanols or oxyalkanols, said alkanols having about 7 to 20 carbon atoms.

12. The process of claim 11, wherein the components I and II of said composition are the product obtained by reacting an alcohol of the group defined with P$_2$S$_5$ first to form O,O-disubstituted dithiophosphoric acid until most of the P$_2$S$_5$ has dissolved and the evolution of H$_2$S has subsided and then continuing the reaction to shift the equilibrium in favor of converting said O,O-substituted dithiophosphoric acid to the pyrophosphates, and the components III of said composition are prepared by reacting an alcohol of the group defined with P$_2$O$_5$ or polyphosphoric acid.

13. The process of claim 11, wherein the components I and II of said composition are those obtained by reacting an alcohol of the group defined with P$_2$S$_5$ first to form O,O-disubstituted dithiophosphoric acids until most of the P$_2$S$_5$ has dissolved and the evolution of H$_2$S has subsided, then continuing the reaction to shift the equilibrium in favor of converting said O,O-disubstituted dithiophosphoric acids to the pyrophosphates and converting said disubstituted dithiophosphoric acids to salts, and the components III of said composition are prepared by reacting the alcohol of the group defined with P$_2$O$_5$ or polyphosphoric acid.

14. The process of claim 11, where the composition also contains zinc ions.

* * * * *